United States Patent [19]

Hanifl

[11] 4,404,881
[45] Sep. 20, 1983

[54] NEEDLE AND SYRINGE DESTRUCTOR

[75] Inventor: Paul H. Hanifl, Barrington, Ill.

[73] Assignee: Sage Products, Inc., Cary, Ill.

[21] Appl. No.: 294,326

[22] Filed: Aug. 19, 1981

[51] Int. Cl.³ .................. B23D 15/00; B26D 5/10
[52] U.S. Cl. ................................. 83/167; 83/580;
83/618; 83/633; 83/635; 83/925 R
[58] Field of Search ............... 83/167, 580, 618, 633,
83/635, 925 R

[56] References Cited
U.S. PATENT DOCUMENTS

| | | | |
|---|---|---|---|
| 3,404,593 | 10/1968 | Arcarese et al. | 83/167 |
| 3,469,750 | 9/1969 | Vanderbeck | 83/167 X |
| 3,585,835 | 6/1971 | Clement | 83/167 X |
| 3,736,824 | 6/1973 | Dunnican | 83/167 |
| 3,785,233 | 1/1974 | Robinson | 83/167 |
| 3,914,865 | 10/1975 | Oakes | 83/167 X |
| 4,255,996 | 3/1981 | Choksi et al. | 83/167 X |
| 4,275,628 | 6/1981 | Greenhouse | 83/167 |

OTHER PUBLICATIONS

Two Pages of Advertisement for DESTRUCLIP ® Safety Device, Four Pages of Advertisments for HY-POSTRUC TM Mechanical Metal Products, Inc.
Single Page from a Brochure dated Aug. 1974, describing a Pharmaseal Syringe Cutter, Model 9652.

*Primary Examiner*—James M. Meister
*Attorney, Agent, or Firm*—Lee, Smith & Jager

[57] ABSTRACT

A needle and syringe destructor is disclosed having particular suitability for the destruction of hypodermic syringe needles, of the single-use variety, immediately after use. The needle, and a portion of the syringe barrel, may be simultaneously severed in a single motion by means of the operator actuating a lever arm means. The lever arm means is linked to a pair of guillotine shears effectuating severance with increased mechanical advantage to the operator. Severed portions drop to a storage chamber. Remaining syringe barrel portions may then be discarded into the storage chamber through a movable closure lid providing separate access to the storage chamber. The severed needle and syringe are destroyed to prevent re-use and accidental injury to medical personnel.

16 Claims, 10 Drawing Figures

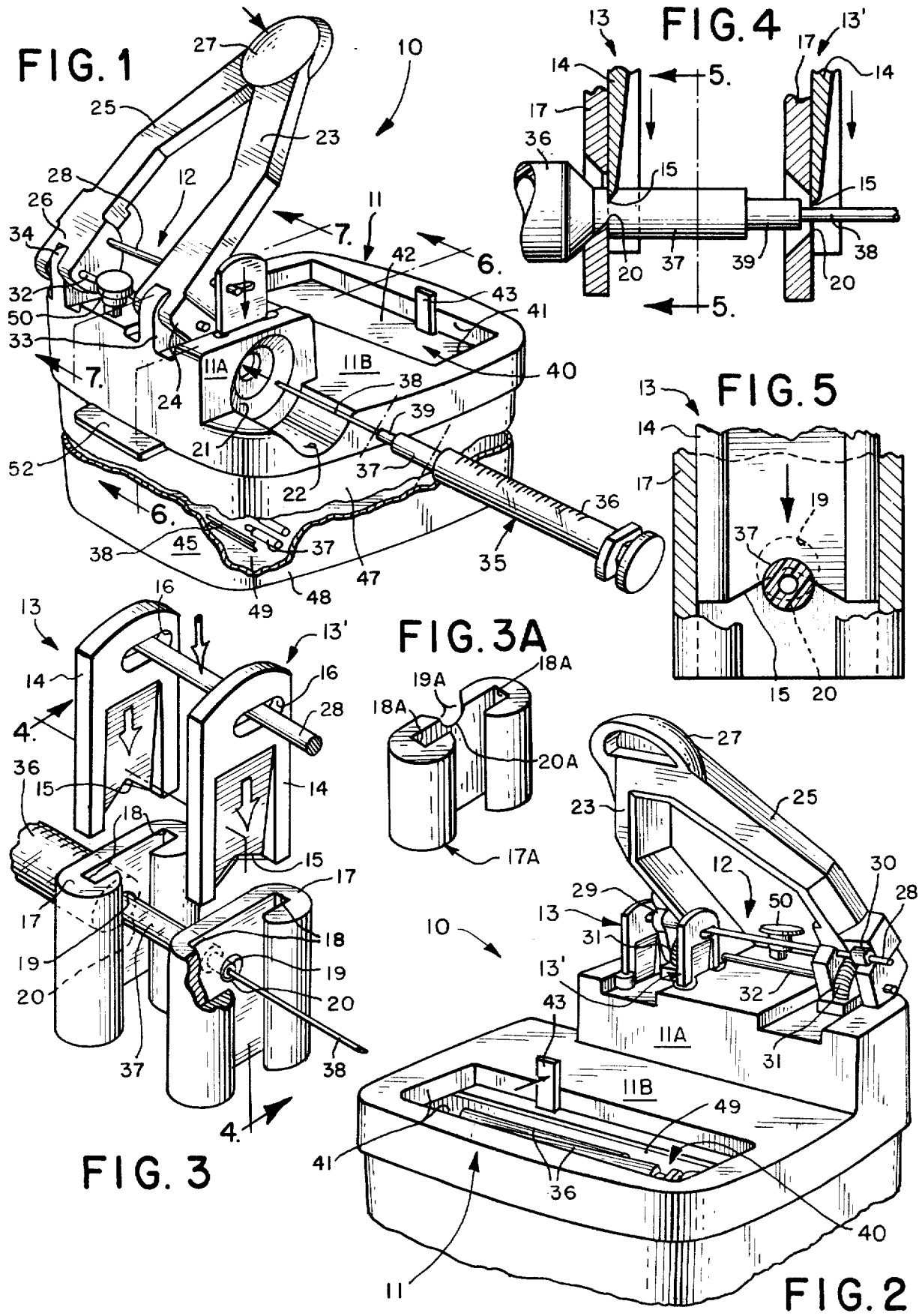

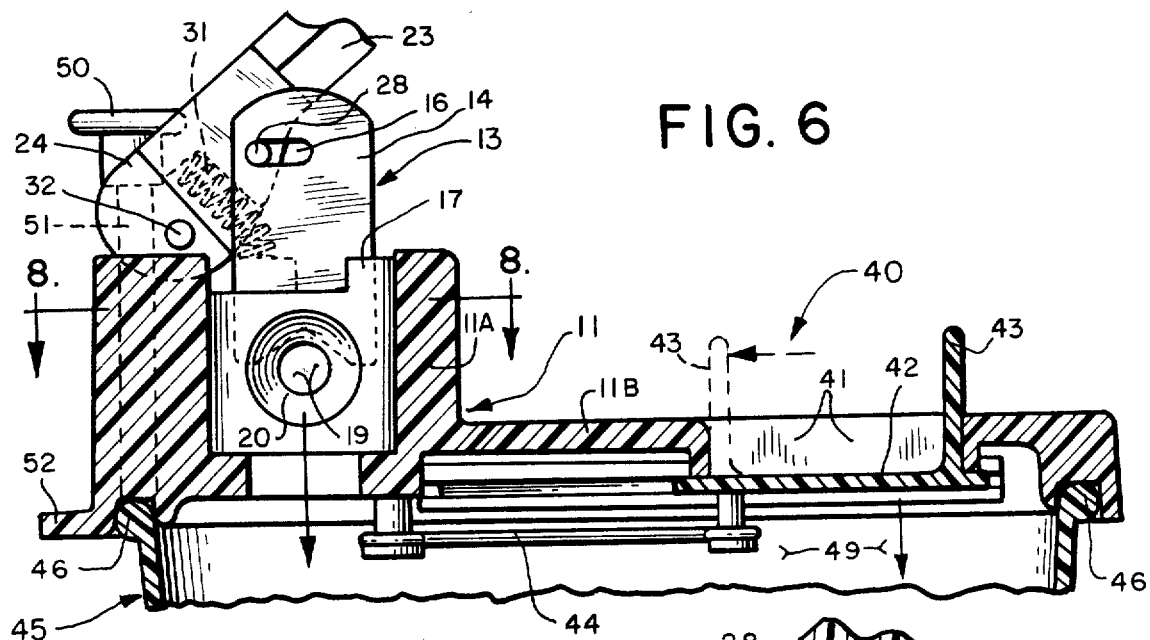
FIG. 6
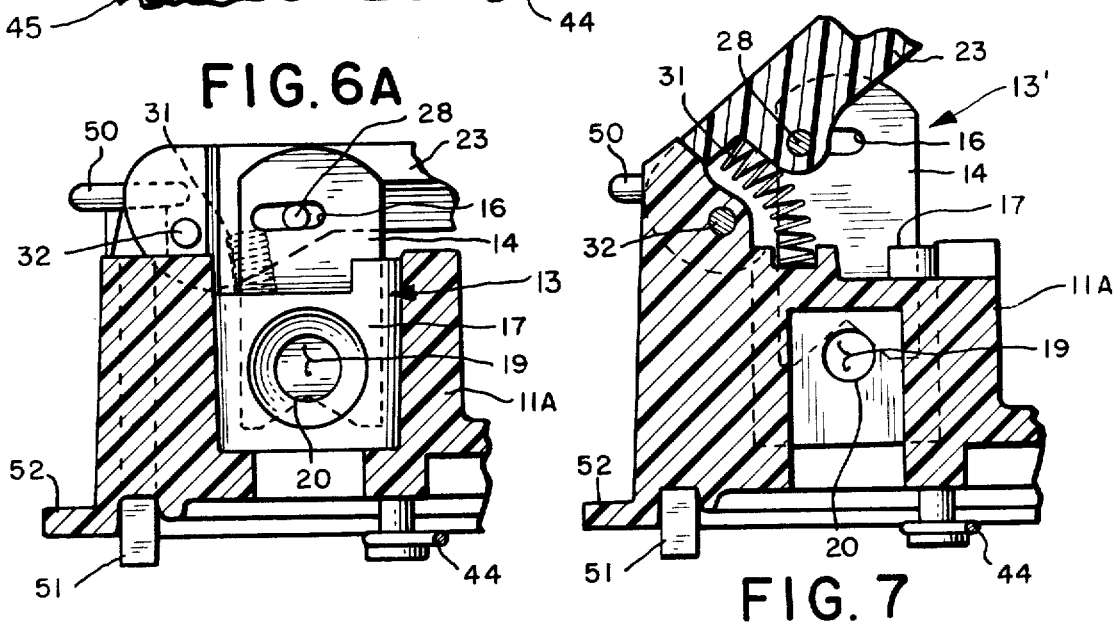
FIG. 6A
FIG. 7
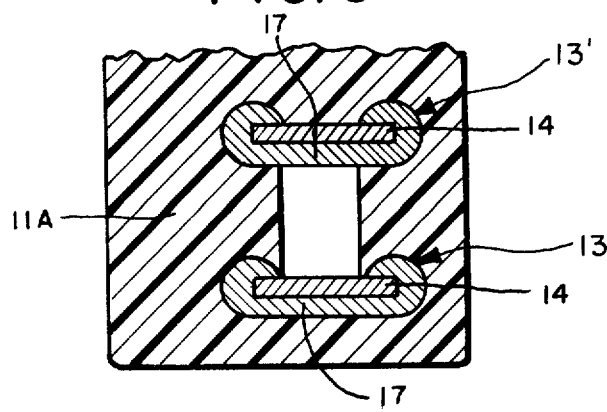
FIG. 8

NEEDLE AND SYRINGE DESTRUCTOR

BACKGROUND AND SUMMARY OF THE INVENTION

The invention relates to a device for prompt and safe destruction of needles and syringes immediately after use to thereby prevent illegal re-use and drastically diminish the possibility of accidental injury to medical personnel.

The ultimate disposal of used hypodermic syringes has been a constant concern in the medical field. Existing techniques and devices for needle destruction include dual devices which sever a cannular needle and also sever the needle hub, or a portion of the syringe barrel adjacent the needle hub. It is the purpose of this invention to significantly advance dual severance techniques with an easily used device that offers mechanical advantage to the operator, safe use, balanced leverage, and provision for storing a large number of destroyed needles and syringe barrels.

Many previous dual severing devices do not offer the ability to easily replace used cutting means. The instant invention additionally allows for the replacement of cutting portions after long use. In operation, the needle and syringe destructor of the present invention allows the operator to direct the needle in a safe manner away from himself and into a selected position where the needle and syringe are prepared from the simultaneous dual severing. The severed portions of the used needle and syringe drop harmlessly into a storage container. The remaining barrel may be quickly disposed of by separately dropping the barrel through a closure lid which is provided in the same storage container.

Many prior devices require that the user hand-hold the device, which can lead to an unsafe disposition of the sharp end of a cannular needle. In the instant invention the destructor may be stationed on a table or other flat surface, and by action of a lever arm means a downward movement against the flat surface provides a very sure and steady cutting maneuver, with the needle in safe and secure disposition as it is being severed.

The major portion of the destructor is preferably formed of high impact plastic material and only a minimal amount of more costly metal components. Yet, with the utilization of a molded plastic, the invention affords significant mechanical advantage in accomplishing its tasks.

The destructor also provides a sufficiently sized opening and access to shearing means, hereinafter described, whereby a wide variety of syringes and needles may be inserted and destroyed.

BRIEF DESCRIPTION OF THE DRAWINGS

Further objects and features of the present invention will become apparent from the following description of the accompanying drawings.

FIG. 1 is a perspective view of the needle and syringe destructor in one embodiment for the invention, showing a hypodermic syringe needle ready for insertion and destruction.

FIG. 2 is a perspective front view of the embodiment shown in FIG. 1.

FIG. 3 illustrates the shear blades for the first embodiment of the invention in perspective and exploded view, with a hypodermic syringe needle disposed for severance.

FIG. 3A illustrates a second embodiment for a static shear blade of the invention.

FIG. 4 is a sectional view taken along lines 4—4 of FIG. 3 looking in the direction of the arrows and showing the components assembled and ready for destruction of the hypodermic syringe needle.

FIG. 5 is a view taken along lines 5—5 of FIG. 4 looking in the direction of the arrows illustrating the shearing action of the shear blades at the collar of a syringe barrel.

FIG. 6 is a cross-sectional view of FIG. 1 taken along line 6—6 looking in the direction of the arrows illustrating one pair of shear blades of the shearing means in retracted position ready for the insertion of a hypodermic needle.

FIG. 6A is a portion of the cross-sectional view shown in FIG. 6 illustrating the shear blades at completion of a downward shearing motion.

FIG. 7 is a cross-sectional view of FIG. 1 taken along line 7—7 looking in the direction of the arrows and showing the other pair of shear blades in retracted position.

FIG. 8 is a cross-sectional view of FIG. 6 taken along lines 8—8 looking in the direction of the arrows, showing the pair of guillotine shears.

DETAILED DESCRIPTION OF THE ILLUSTRATED EMBODIMENTS

FIGS. 1 and 2 show needle and syringe destructor 10 in perspective views, first looking from the rear and then from the front respectively. Destructor 10 has a portable size for use on a table top or other flat surface facilitating safe and sure positioning during destruction of syringes and needles.

Destructor 10 comprises a base 11 having a first portion 11A and a second portion 11B. Base 11 is mounted on the top of a receptacle 45 for disposition of destroyed needles and syringes. First portion 11A includes shearing means 12 which provides the means for needle and syringe severing. Second portion 11B includes disposal means 40 for deposit of severed syringe barrels into receptacle 45 subsequent to severance at shearing means 12.

First portion 11A can be generally described as a raised housing portion on base 11, and second portion 11B as having a generally planar, or plate-like configuration which includes disposal means 40.

With reference to FIGS. 3-5, shearing means 12 includes a pair of guillotine shears 13 and 13'. The shears are substantially identical, but are spaced apart for severance at two cutting locations. Guillotine shears 13 and 13' each include a movable shear blade 14 having a shearing edge 15 preferably of a V-shaped configuration. A linkage slot 16 is provided upwardly from shearing edge 15, which purpose will be later explained. Cooperative with each movable shear blade 14 is a static shear blade 17. The blades 17 are mounted in a stationary position within first portion 11A, and including opposing guide grooves 18 for sliding engagement with movable blade 14. Static shear blade 17 includes access aperture 19 for syringe and needle entry. Access aperture 19 has a peripheral edge including a cutting edge 20.

Guillotine shears 13 and 13' reside substantially parallel within first portion 11A. Access apertures 19 in the two static shear blades 17 align co-axially. Admittance to guillotine shears 13 and 13' is achieved through entry portal 21 comprising an opening through first portion 11A generally adjacent shear 13 and co-aligned with access apertures 19. Entry portal 21 and access apertures 19 each desirably have a funnel-shape for expeditious insertion of a syringe and needle, such as hypodermic needle 35 as shown. To further facilitate positioning for severance, recess 22 extends adjacent entry portal 21 to cradle the cylindrical shape of syringe barrels such as barrel 36.

Movable shear blades 14 are movable in close tolerance with static shear blades 17 as can be seen when viewing FIG. 4. Shearing edges 15 on the blades 17 traverse access apertures 19 and move closely past cutting edges 20. This close tolerance movement results in effective shearing of hypodermic needle 35.

For the purpose of describing utilization of destructor 10, hypodermic needle 35 is shown as a well-known single-use type. Hypodermic needle 35 includes a barrel 36 terminating in a necked collar 37 which associates with cannular needle 38 at needle hub 39. In the illustrative embodiment, needle hub 39 is friction-fit to necked collar 37. The cut lines, as shown by the dotted lines in FIG. 1, denote the severance planes in which guillotine shears 13 and 13' slice. The cannular needle 38 is severed to preclude re-use, and barrel 36 is destroyed at necked collar 37 to prevent adaptation for further usage. The V-shapes desirable for shearing edges 15 aid in holding the hypodermic needle in a secured position while further exerting a wedge-like cutting action as the needle and barrel pportions of the needle 35 contact the narrowing cutting edge gap leading to the apex of the V. The preferable included angle for V-shaped shearing edge 15 is about 120°.

Shearing means 12 includes a hand manipulable lever means to afford ease of severance to the operator. In the preferred embodiment the lever means comprises two lever arms 23 and 25. An end of arm 23 includes clevis 24 for hinging purposes later described. Arm 25 similarly includes a substantially identical clevis 26. Arms 23 and 25 join at handle 27. A generally symmetric lever means is accordingly provided which offers the operator a balanced and stable feel while exerting downward force at handle 27. While dual arm lever means construction is preferred, it would be clear that a single lever arm, such as arm 23 alone, would satisfy syringe and needle shearing. Arms 23 and 25 are linked to movable shear blades 14 by connector means comprising rod member 28. Rod member 28 is carried by arms 23 and 25 at attachment means comprising apertures 29 and 30. Rod member 28 movably engages linkage slots 16 such that actuation of the lever means imparts motion to movable shear blades 14. Thus, downward movement by the operator at handle 27 imparts the shearing action for shearing means 12.

In the embodiment shown, rod member 28 is removable by pulling sideways to disengage linkage slots 16 and apertures 29 and 30. When the rod member 28 is removed, movable shear blades 14 are unlinked from the lever means, permitting the replacement, or interchangeability, of the shear blades. Removal of the blades 14 is attained by pulling the shear blades from engagement with opposing guide grooves 18 in an upward direction, away from access apertures 19.

It will be apparent that as movable shear blade 14 moves downwardly, with shearing edge 15 traversing access aperture 19, upwardly directed portions of edge 20 opposingly act in co-operation with the shear blade 14 to sever hypodermic needle 35. Accordingly, access apertures 19 need not include a continuous peripheral edge with cutting edge 20, such as the circular configuration of the preferred embodiment shown in FIGS. 3 and 4. One alternate embodiment is an upwardly open, or generally semi-circular configuration, illustrated in the alternate preferred embodiment of FIG. 3A. There, static shear blade 16A includes opposing guide grooves 18A. Access aperture 19A, rather than having a closed continuous peripheral edge, has a generally semi-circular conformation in opposing direction, for cooperation with a movable shear blade. Other suitable shearing shapes for access apertures could include a V-shape, similar to V-shaped cutting edge 15, as would be clear to one skilled in the art.

Lever arm means 23 and 25 are pivotal about hinge means comprising shaft 32 extending through clevises 24 and 26 and posts 33 and 34, which are formed on first portion 11A. Clevises 24 and 26 are freely rotational, and allow the lever means to pivot about the axis of shaft 32.

As pivoting rotation is imparted by the operator moving handle 27 downward, the opposing guide grooves 18 restrain movable shear blades 14 to a vertical shearing motion. The leverage provided by arms 23 and 25 gives mechanical advantage to the operator. Further, as described in more detail below, additional mechanical advantage is provided by means of the motion of the rod member 28 movable within linkage slot 16.

Substantially identical springs 31 bias lever arms 23 and 25 upwardly to a retracted position after use to position movable shear blades 14 upward from access apertures 19 and permit entry of a next needle and syringe. In the preferred embodiment springs 31 are each straddled by clevises 24 and 26.

As movable shear blades 14 traverse access apertures 19, shearing edge 15 slices past cutting edge 20 in close proximity for effective severance of hypodermic needle 35 at cannular needle 38 and at necked collar 37. Severed portions, segmented at the cut lines in FIG. 1, then drop from shearing means 12 downwardly. Base 11 is re.novably associated with receptacle 45, and receptacle 45 opens upwardly to first portion 11A and second portion 11B. Therefore, the dropping severed pieces of a needle and syringe fall directly into receptacle 45.

Remaining portions of barrel 36, which could be hand-held during positioning and severance, may separately be deposited into receptacle 45 at disposal means 40 included in second portion 11B. Disposal means 40 comprises an opening 41 and a movable closure lid means 42. Lid means 42 allows selective access to opening 41 by manual movement of tab 43. Closure is maintained by the provision of spring means 44, best shown in FIG. 6. Spring means 44 reiliently biases lid means 42 to a closed position for a safe containment of used needle portions within the receptacle 45.

With further reference to FIG. 6, it will be seen that receptacle 45 includes a peripheral edge 46 which removably engages extremities of base 11. Side wall portions 47 and lower wall 48 form bounds defining storage chamber 49 into which severed portions of hypodermic needle 35 fall from shearing means 12 and disposal means 40. Receptacle 45, in the preferred embodiment, has a convenient size approximately six inches high and six inches square allowing for a significant quantity of destroyed syringes and needles to be stored. The invention affords an additional benefit in that deposits of barrels 36 through opening 41 can be made in a horizontal fashion. This avoids a vertical stacking of destroyed syringes and needles which otherwise might cause obstructions during the severing procedures and present a potential hazard to the operator when the lid 42 is opened.

With respect to FIGS. 6 and 6A, base 11 can be readily removed from receptacle 45, when it is filled, by action of release means detaching peripheral edge 46 from base 11. The release means comprises a button 50 having depending pin 51 slidably engaging an aperture in the first portion 11A, generally above peripheral edge 46 (See FIG. 6). At engagement, pin 51 sits atop peripheral edge 46 with button 50 extending upwardly. First portion 11A is formed with extension 52 generally adjacent button 50. The operator can depress button 50, to thereby force pin 51 to butt against peripheral edge 46 for release of base 11 from receptacle 45. The operator can additionally grasp extention 52 while depressing button 50 to aid in disengagement. Receptacle 45 can then be emptied to a refuse container, or the like, for ultimate needle and syringe disposal, and then base 11 can be re-attached to receptacle 45 for continuing utilization. Optionally, a separate solid lid could be provided to cover a filled receptacle 45 for disposal and a new replacement receptacle can be attached to base 11.

FIGS. 6, 6A and 7, being cross-sectional views of destructor 10, show additional details with sections taken along lines 6—6 and 7—7 in FIG. 1. It will be noted that shearing means 12 permits severed portions to drop directly downwardly into storage chamber 49, as indicated by the arrow in FIG. 6. Similarly, the sliding motion of movable closure lid means 42 allows the operator to drop the remaining portions of barrel 36 into storage container 49 subsequent to severance. The horizontal motion of lid 42 allows the lid to be opened without interference with the severed parts in the storage chamber 49. FIGS. 6 and 6A specifically show the traversal of movable shear blade 14 with shearing edge 15 past cutting edge 20 to effectuate severance. FIGS. 6 and 6A depict guillotine shear 13 which is adjacent entry portal 21 and would sever necked collar 37. FIG. 7 depicts guillotine shear 13' which would sever cannular needle 38. Also, as seen when also viewing FIG. 8, guillotine shears 13 and 13' are spaced-apart a distance sufficient to accommodate conventional sizes, such as hypodermic syringe needle 35. Simultaneous dual shearing at the cut lines shown in FIG. 1 is thereby attained. The diameters, or opening dimensions, of entry portal 21 and access apertures 19 are also significantly large to accommodate a variety of needle hub and barrel dimensions. A broad spectrum of syringes and needles therefore can be destroyed by use of the present invention.

Additional mechanical advantage is provided by destructor 10 with the movement of rod number 28 from a back position, as shown in FIG. 6, to a forward position as shown in FIG. 6A. Rod member 28 moves in an arc rotating about hinge means shaft 42 while movable shear blade 14 is restrained to a vertical path by opposing guide grooves 18. Rod member 28 creates a wedging or camming action against the bottom surface of linkage slot 16 as it moves to a central blade location within linkage slot 16, as shown in FIG. 6A. This permits the operator to create a direct vertical shear force over the central vertical axis of movable shear blade 14. Accordingly, severance of hypodermic needle 35 along the two cut lines shown in FIG. 1 is readily accomplished without the application of undue manual force. The utilization of two lever arms 23 and 25 facilitates symmetric balanced application of leverage force exerted by the operator between posts 33 and 34.

FIG. 7 shows guillotine shear 13' in a relaxed biased-upward, or retracted, state with springs 31 urging lever arms 23 and 25 upwardly, following release of handle 27 by the operator. FIG. 6A further shows button 50 downward with pin 51 extending downward below extension 52 in a release position whereby disengagement with peripheral edge 46 is obtained.

FIG. 8 is a cross-sectional view of guillotine shears 13 and 13'. First portion 11A includes shearing means 12 whereby static shear blades 17 are mounted within molded recesses of the generally housing-like conformation of first portion 11A. The close tolerance fit between movable shear blades 14 and static shear blades 17 is depicted. In the preferred embodiment movable shear blades 14 are movably retained in the aforementioned generally vertical path, as is evident from the detailed cross-section FIG. 8.

Destructor 10 is primarily comprised of high impact plastic which is lightweight and portable, and which can be made with relatively low manufacturing and material costs. Few metal components are required. It is preferable that guillotine shears 13 and 13' comprise hardened steel for long cutting edge life and endurance. Rod member 28 is desirably comprised of steel to achieve the aforementioned mechanical advantage during actuation of the lever means. Similarly the hinge means desirably includes a steel shaft 32 for strength and long use. The resilient biasing provided by springs 31 and spring means 44 is successfully achieved using steel springs, but other resilient material achieving the same function may be adapted for the invention. While spring 31 preferably has a helical coil shape other suitable spring configurations, such as a leaf spring, may equally be suited for implementation in the invention. Similarly spring means 44 may include other well known spring configurations other than the wire-like member shown in the drawings.

Lever arms 23 and 25 need not be metal and are preferably also formed of high impact plastic, to further afford a relatively economic construction while yet giving the desirable mechanical advantage.

The lever means, including lever arms 23 and 25 joining at handle 27, may comprise alternative embodiments. For example, only one lever arm could be provided which could be centrally located with respect to first portion 11A to maintain overall balance in using destructor 10. In such an alternative the single lever arm may be a straight arm terminating in a handle at the end opposite hinge means. Such modifications will be clear to one skilled in the mechanical arts.

It is therefore apparent that there has been provided, in accordance with the invention, a needle and syringe destructor that fully satisfies the objects, aims and advantages set forth. While the invention has been described in conjunction with specific embodiments thereof, it is evident that many alternatives, modifications and variations will be apparent to those skilled in the art in light of the foregoing description. Accordingly, it is intended to embrace all such alternatives, modifications, and variations as fall within the spirit and broad scope of the appended claims.

What is claimed is:

1. A needle and syringe destructor comprising:
    a base having a first portion including shearing means and a second portion including disposal means;
    said shearing means comprising a pair of guillotine shears each having a movable shear blade and a static shear blade, said movable shear blades having a shearing edge and a linkage slot, said static shear blades having opposing guide grooves accommodating said movable shear blades and each having an access aperture both being coaxial and each having a static shearing edge capable of shearing association with a movable shear blade, a connector means movably engaging the linkage slots of said movable shear blades, a lever arm means in pivotal relationship with said first base portion at hinge means and having attachment means engaged with said connector means linking said lever arm means with said guillotine shears, entry portal means coaxial with said access apertures opening adjacent to a guillotine shear and opening outwardly of said first base portion, said disposal means comprising
an opening in said second base portion,
a movable closure lid associating with said opening,
a receptacle having a peripheral edge associating with said base in removable relationship, an open side defined by said peripheral edge opening to said first and second base portions, and sidewall and lower wall portions defining a containment chamber therebetween, wherein a needle and syringe is insertable through said entry portal means for positioning of a needle at one of the guillotine shears and a portion of a syringe barrel at the other, whereupon said lever arm is hand manipulable to actuate said movable shear blades to traverse across access apertures of said static shear blades whereby the needle and syringe barrel are severable in one traversal, whereupon severed portions enter said containment chamber and remaining syringe barrel portions extending outwardly of said entry portal means may be deposited at said disposal means through said opening by opening said movable closure lid and depositing such portions into said containment chamber of said receptacle.

2. A needle and syringe destructor as claimed in claim 1 wherein said shearing edges of said movable shearing blades are V-shaped.

3. A needle and syringe destructor as claimed in claim 1 wherein said static shearing edges of said static shear blades define peripheral edges of said access apertures.

4. A needle and syringe destructor as claimed in claim 3 wherein said static shearing edge is formed with a continuous peripheral edge of said access aperture.

5. A needle and syringe destructor as claimed in claim 4 wherein said access aperture is discontinuous having a periphiral edge disposed in a direction toward said movable shearing blade.

6. A needle and syringe destructor as claimed in claim 1 wherein said guillotine shears comprise hardened steel.

7. A needle and syringe destructor as claimed in claim 1 wherein said entry portal means is funnel-shaped.

8. A needle and syringe destructor as claimed in claim 7 wherein said access apertures of said static shear blades are funnel-shaped.

9. A needle and syringe destructor as claimed in claim 1 wherein said lever arm means associates with resilient biasing means capable of biasing said lever arm means to a retracted position facilitating insertion of a needle and syringe.

10. A needle and syringe destructor as claimed in claim 1 wherein said movable closure lid includes spring means resiliently biasing said lid to a closed position.

11. A needle and syringe destructor as claimed in claim 1 wherein said first base portion includes release means adapted to disengage said base portion from said receptacle along said peripheral edge.

12. A needle and syringe destructor capable of simultaneous dual severing of a syringe and needle in a single motion by the operator wherein severed portions safely fall to a storage chamber and wherein a remaining severed syringe barrel portion may be deposited separately into said storage chamber, said destructor comprising:

a pair of guillotine shears operable in response to an associated lever arm means, said guillotine shears and lever arm means linked by movable connector means supplying mechanical advantage to the operator, said guillotine shears and lever arm means included in a base portion having an entry portal facilitating access to said guillotine shears and hinge means pivotally connecting said lever arm means to said base portion, said guillotine shears each comprising a movable shear blade movable downward to traverse past a cutting edge of a static shear blade by means of operation of said lever arm means, said movable shear blade residing in guide grooves of said static shear blade for close positioning of said blades to effectuate shearing action, said guillotine shears being spaced-apart a sufficient distance whereby a syringe and needle can be positioned with a needle at one guillotine blade and a syringe barrel portion at the other guillotine shear, said base portion removably fastened to a storage container means having a storage chamber opening to said guillotine shears whereby severed needles and syringe portions may fall safely into said storage chamber upon severance, said base portion further having disposal means including a closure lid means movably opening to said storage chamber whereby remaining severed syringe barrel portions may be discarded into said storage chamber following severance.

13. A needle and syringe destructor as claimed in claim 12 wherein said lever arm means associates with resilient biasing means urging said lever arm means to a retracted position facilitating insertion of a needle and syringe into the destructor.

14. A needle and syringe destructor as claimed in claim 12 wherein each said static shear blade includes an access aperture, at least a portion of which comprises said cutting edge, cooperative with said movable shearing blades and wherein said access apertures are coaxial with said entry portal of said base portion.

15. A needle and syringe destructor as claimed in claim 12 wherein said movable connector means comprises a rod member connecting said lever arm means to said movable shear blades.

16. A needle and syringe destructor as claimed in claim 15 wherein said movable shear blades include a linkage slot movably engaged by said rod member.

* * * * *